(12) United States Patent
O'Brien et al.

(10) Patent No.: US 9,113,798 B2
(45) Date of Patent: Aug. 25, 2015

(54) METHOD AND APPARATUS FOR VETERINARY CT SCANS

(75) Inventors: Robert T. O'Brien, Champaign, IL (US); Gerald J. Pijanowski, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 594 days.

(21) Appl. No.: 13/170,311

(22) Filed: Jun. 28, 2011

(65) Prior Publication Data

US 2012/0027167 A1    Feb. 2, 2012

Related U.S. Application Data

(60) Provisional application No. 61/368,391, filed on Jul. 28, 2010.

(51) Int. Cl.
A61B 6/04    (2006.01)
A61B 6/03    (2006.01)
A61B 6/00    (2006.01)

(52) U.S. Cl.
CPC . *A61B 6/032* (2013.01); *A61B 6/04* (2013.01); *A61B 6/508* (2013.01); *A61B 6/583* (2013.01)

(58) Field of Classification Search
CPC .......... A61B 6/032; A61B 6/04; A61B 6/508; A61B 6/583
USPC ............................. 378/208, 65, 64, 68, 57, 58
See application file for complete search history.

(56) References Cited

U.S. PATENT DOCUMENTS

| | | | |
|---|---|---|---|
| 6,857,778 B2 * | 2/2005 | Mun et al. ..................... | 378/206 |
| 7,767,990 B2 * | 8/2010 | Cadwalader et al. ...... | 250/519.1 |
| 8,276,225 B2 * | 10/2012 | Kogan et al. ..................... | 5/601 |
| 2007/0181075 A1 * | 8/2007 | Conger et al. ................ | 119/458 |
| 2009/0080600 A1 * | 3/2009 | Keller et al. .................... | 378/18 |
| 2009/0199360 A1 * | 8/2009 | Madanat ......................... | 16/111.1 |
| 2010/0067659 A1 * | 3/2010 | Bush ............................... | 378/68 |
| 2010/0206287 A1 * | 8/2010 | McLemore et al. .......... | 126/1 R |

OTHER PUBLICATIONS

Luca Salvolini, Elisabetta Bichi Secchi, Leonardo Costarelli, Maurizio De Nicola. European Journal of Radiology, vol. 34, Issue 1, Apr. 2000, pp. 9-25.*
Deborah J. Shumaker, Michael F. McNitt-Gray, Carolyn Kimme-Smith, Keyvan Farahani. SPIE Conference on Physics of Medical Imging. San Diego, Feb. 1999, p. 603-613.*
K. Scarabello. Invention helps vets with emergency cat care. The Daily Illini, Dec. 7, 2009.*
C. Beuoy-Illinois. 'Cat' Scan Without Anesthesia. Futurity: Discover the Future, Feb. 18, 2010 published online in http://www.futurity. org/.*

(Continued)

*Primary Examiner* — Hoon Song
(74) *Attorney, Agent, or Firm* — Dilworth IP LLC

(57) ABSTRACT

A substantially X-ray transparent animal restraint enclosure having an open base structure and a lid which is configured to substantially close the base structure. The lid is movable from a closed position to an open position to permit the introduction of an animal into the base structure. The base structure has an open-ended slot which is partially obstructed when the lid is closed. The base structure also has an aperture which is not obstructed by the lid. A veterinary CT scan apparatus includes a CT scan gantry or sensor ring, a CT scan table, and a substantially X-ray transparent animal restraint enclosure. A method of performing a CT scan on an animal in a CT scan apparatus having a patient target position is achieved by placing the animal in substantially X-ray transparent enclosure; placing the enclosure in the patient target position for the CT scan; and conducting the CT scan.

7 Claims, 3 Drawing Sheets

(56) References Cited

OTHER PUBLICATIONS

Goldman, Lee W., "Principles of CT and CT Technology", Journal of Nuclear Medicine Technology vol. 35, No. 3 Sep. 2007, 115-128.

Burk, R. L., "Computed Tomography of Thoracic Diseases in Dogs", J. Am. Vet. Med. Assoc. vol. 199, No. 5 Sep. 1991, 617-621 (copy unavailable).

Johnston, Cynthia et al., "Atelectasis in children: mechanisms, diagnosis and treatment", Brazilian Journal of Medicine Rev. Assoc. Bras Med. vol. 54, No. 5 Oct. 2008 (translated version enclosed).

Paulson, Erik K. et al., "MDCT of Patients with Acute Abdominal Pain: A New Perspective using Coronal Reformations from Submillimeter Isotropic Voxels", AJR:183 Oct. 2004, 899-906.

Polacin, A. et al., "Evaluation of section sensitivity profiles and image noise in spiral CT", Radiology vol. 185 Oct. 1992, 29-35 (abstract only).

Kalva, MD Sanjeeva P., "Using the K-edge to Improve Contrast Conspicuity and to Lower Radiation Dose with a 16-MDCT: a Phantom and Human Study", J. Comput. Asst. Tomogr. vol. 30, No. 3 May, Jun. 2006, 391-397.

Mori, I., "Antialiasing backprojection for helical MDCT", American Association of Physicists in Medicine Med. Physc. 35 (3) Mar. 2008, 1065-1077.

Szucs-Farkas, MD, Zsolt et al., "Effect of X-ray Tube parameters, Iodine Concentration, and Patient Size on Image Quality in Pulmonary Computed Tomography Angiography: A Chest-Phantom-Study", Investigative Radiology vol. 43, No. 6 Jun. 2008, 374-381.

Florh, Phd, Thomas G. et al., "Multi-Detector Row CT Systems and Image-Reconstruction Techniques", Radiology vol. 235, No. 3 Jun. 2005, 756-773.

Pappas, MD, John N. et al., "Reduced Frequency of Sedation of Young Children with Multisection Helical CT", Radiology, Duke University Medical Center vol. 215, No. 3 Jun. 2000, 897-899.

Dalrymple, MD, Neal C. et al., "Price of Isotropy in Multidetector CT", RadioGraphics vol. 27, No. 1 Jan.-Feb. 2007, 49-62.

Viera, MD, Anthony J. et al., "Understanding Interobserver Agreement: The Kappa Statistic", Family Medicine Robert Wood Johnson Clinical Scholars Program, University of North Carolina May 2005, 360-363.

Stadler, Krystina et al., "Computed Tomographic Imaging of Dogs with Primary Laryngeal or Tracheal Airway Obstruction", Department of Veterinary Clinical Medicine, University of Illinois at Urbana-Champaign 2011, 1-9.

Oliveira, Cintia R. et al., "Thoracic Computed Tomography in Feline Patients Without Use of Chemical Restraint", Department of Veterinary Clinical Medicine, University of Illinois at Urbana-Champaign 2011, 1-9.

Oliveira, Cintia R. et al., "The VetmouseTrap (TM): A Device for Computed Tomographic Imaging of the Thorax of Awake Cats", Department of Veterinary Clinical Medicine, University of Illinois at Urbana-Champaign 2010, 1-12.

Joly, Hugo et al., "Comparison of Single-Slice Computed Tomography Protocols for Detection of Pulmonary Nodules in Dogs", Veterinary Radiology and Ultrasound vol. 50, No. 3 2009, 279-284.

Drees, Randi et al., "Computed Tomographic Imaging Protocol for the Canine Cervical and Lumbar Spine", Veterinary Radiology & Ultrasound vol. 50, No. 1 2009, 74-79.

Ohlerth, Stefanie et al., "Computed tomography in small animals—Basic principles and state of the art applications", Science Direct, The Veterinary Journal 173 2007, 254-271.

Nemanic, Sarah et al., "Comparison of Thoracic Radiographs and Single Breath-Hold Helical CT for Detection of Pulmonary Nodules in Dogs with Metastatic Neoplasia", J. Vet. Intern. Med. vol. 20 2006, 508-515.

Rydberg, J. et al., "Isotropic Chest CT Examination: Diagnostic Quality of Reformats", Department of Radiology, Indiana University School of Medicine vol. 61 2006, 588-592.

Zamyatin, Alexander A. et al., "Up-sampling with Shift Method for Windmill Correction", IEEE Nuclear Science Symposium Conference Record 2006, 2293-2295.

Berent, Allyson C. et al., "Carbon monoxide toxicity: a case series", Journal of Veterinary Emergency and Critical Care vol. 15, No. 2 2005, 128-135.

Prather, Andrew B. et al., "Use of Radiography in Combination with Computed Tomography for the Assessment of Noncardiac Thoracic Disease in the Dog and Cat", Veterinary Radiology & Ultrasound vol. 46, No. 2 2005, 114-121.

Barrett, MSC, Julia F. et al., "Artifacts in CT: Recognition and Avoidance", RadioGraphics vol. 24 2004, 1679-1691.

Yoon, DVM, PhD, Junghee et al., "Computed Tomographic Evaluation of Canine and Feline Mediastinal Masses in 14 Patients", Veterinary Radiology & Ultrasound vol. 45, No. 6 2004, 542-546.

Sigal-Cinqualbre, MD, Anne B. et al., "Low-Kilovoltage Multi-Detector Row Chest CT in Adults: Feasibility and Effects on Image Quality and Iodine Dose", Radiology 2004 vol. 231 2004, 169-174.

Johnson, V. S. et al., "Thoracic High-Resolution Computed Tomography in the Diagnosis of Metastatic Carcinoma", Journal of Small Animal Practice vol. 45 2004, 134-143.

Rydberg, Jonas et al., "Fundamentals of Multichannel CT", Radiologic Clinics of North America vol. 41 2003, 465-474.

Henninger, W., "Use of Computed Tomography in the Diseased Feline Thorax", Journal of Small Animal Practice 2003, 56-64.

Cipone, M. et al., "Use of Computed Tomography in Thoracic Diseases of Small Animals", Veterinary Research Communications, 27 Suppl. 1 2003, 381-384.

Silver, Michael et al., "Windmill artifact in multi-slice helical CT", Medical Imaging 2003: Image Processing Proceedings of SPIE, vol. 5032 2003, 1918-1927.

Bushberg, Jerrold et al., "The essential physics of medical imaging", 2nd ed. Philadelphia Lippincott Willians and Wilkins 2001 (file too large to upload).

Brody, Alan S. et al., "Thoracic CT Technique in Children", Journal of Thoracic Imaging Vo. 16 2001, 259-268.

Hedenstierna, MD, PhD, Goran et al., "Atelectasis Formation During Anesthesia: Causes and Measures to Prevent IT", J. Clin Monit vol. 16 2000, 329-335.

Novelline, Robert A. et al., "Helical CT in Emergency Radiology", Radiology 1999; vol. 213, No. 2 Department of Radiology, Massachusetts General Hospital 1999, 321-339.

Frush, MD, Donald et al., "Helical CT in Children: Technical Considerations and Body Applications", Radiology Department of Radiology, Division of Pediatric Radiology, Duke University Medical Center 1998, 37-48.

Eisenkraft, JB, "Effects of Anaesthetics on the Pulmonary Circulation.", 669 British Journal of Anaesthesia 65(1) 1990, 63-78 ($1^{st}$ Page only).

Szucs-Farkas, Zsolt et al., "Patient Exposure and Image Quality of Low-Dose Pulmonary Computed Tomography Angiography", Investigative Radiology vol. 43, No. 12 Dec. 2008, 871-876.

White, Charles S. et al., "Chest Pain in the Emergency Department: Role of Multidetector CT", Radiology: vol. 245: No. 3 ''' Dec. 2007, 672-681.

Heyer, MD, Christoph M. et al., "Image Quality and Radiation Exposure at Pulmonary CT Angiography with 100- or 120-kVp Protocol: Prospective Randomized Study", Radiology vol. 245, No. 2 Nov. 2007, 577-583.

Staffieri, DMV, PhD, Francesco et al., "Computed Tomographic Analysis of the Effects of Two Inspired Oxygen Concentrations on Pulmonary Aeration in Anesthetized and Mechanically Ventilated Dogs", American Journal of Veterinary Research vo. 68, No. 9 Sep. 2007, 925-931 (abstract only).

Morandi, DVM, MS, Federica et al., "Correlation of Helical and Incremental High-Resolution Thin-Section Computed Tomographic Imaging with Histomophometric Quantitative Evaluation of Lungs in Dogs", American Journal of Veterinary Research vol. 64, No. 7 Jul. 2003, 935-944 (abstract only).

Mann, F. A. et al., "Transcutaneous Oxygen and Carbon Dioxide Monitoring in Normal Cats", Journal of Veterinary Emergency and Critical Care vol. 7, No. 2, 99-109.

* cited by examiner

METHOD AND APPARATUS FOR VETERINARY CT SCANS

CROSS-REFERENCE TO RELATED APPLICATION

This application claims the benefit of U.S. provisional application Ser. No. 61/368,391 filed Jul. 28, 2010, entitled "An Apparatus for Restraining Animals," the contents of which are incorporated herein by reference in their entirety.

FIELD OF THE INVENTION

The present disclosure relates generally to an apparatus for facilitating veterinary CT scan procedures by restricting patient movement during the procedures, and to a CT protocol.

BACKGROUND

In humans, computed tomography (CT) is a known diagnostic tool for patients with clinical signs of thoracic disease. Compared with thoracic radiography, CT images have superior contrast resolution and anatomic superposition is not a problem. Pathologic changes that are not apparent on survey radiographs may be detected using CT. CT is also used to differentiate differences between pleural, extrapleural, or mediastinal tissues from that of lung tissue.

When choosing protocols for CT in humans there is always a trade-off between image quality and dosage. Radiologists and technicians must balance protocol selection between resolution, noise, and contrast to achieve good image quality and keep patient exposure as low as reasonably achievable. In pediatric CT there is a recommendation for using a sharper algorithm for reconstruction of lung images. Sharper algorithms delineate object margins more clearly at the expense of increased image noise. Less sharp algorithms reduce noise, allowing larger low contrast object to become more visible although edges will be more blurry and fine detail lost. In veterinary medicine radiation exposure is not as much of a concern as it is in humans, however, studies evaluating radiation dose and safety associated with routine imaging diagnosis are lacking.

In veterinary medicine, survey thoracic radiography is the standard imaging modality used for evaluating the thorax, even though the use of CT to diagnose thoracic diseases in anesthetized cats is known. This is due, at least in part, to the need for general anesthesia when performing CT, because movement by a non-sedated animal patient commonly causes significant artifacts, which usually appear as shading or streaking in the reconstructed image. However, general anesthesia has inherent risks and is sometimes contraindicated in emergency conditions, especially for patients in respiratory distress. General anesthesia often causes varying degrees of atelectasis that can mimic or obscure underlying disease. Additional CT scans in different positions may be necessary to evaluate the patient fully, thereby increasing imaging and anesthesia time.

SUMMARY OF THE INVENTION

The present invention resides in one aspect in a substantially X-ray transparent animal restraint enclosure comprising an open base structure and a lid which is configured to substantially close the base structure when the lid is in a closed position on the base structure. The lid is movable from the closed position to an open position to permit the introduction of an animal patient into the base structure. The base structure has at least one open-ended slot which is partially obstructed when the lid is in the closed position. There is also at least one aperture in the base structure or the lid which is not obstructed when the lid is in the closed position.

In various embodiments, an animal restraint enclosure as described herein may include one or more of the following features: a base structure comprising a base member having a semi-cylindrical configuration and wherein the lid has a semi-cylindrical configuration, so that when the lid is in the closed position, the base member and the lid cooperate to define a substantially cylindrical space, and/or a base structure including a footing for stably supporting the base member on a flat surface. The enclosure may have at least one aperture suitable for providing gas flow through the enclosure. Optionally, the base member has a first base end panel, and a second base end panel, one of the first and second base end panels has a slot therein, the lid has a first lid end panel, and a second lid end panel, and at least one of the first lid end panel and the second lid end panel is configured to partially obstruct the at least one slot in the first and/or second base end panel. In some embodiments, the base structure may include a footing for stably supporting the base member on a flat surface. In one embodiment, the enclosure is substantially visually transparent.

According to another aspect, the present invention provides a veterinary CT scan apparatus comprising: a CT scan gantry or sensor ring, a CT scan table, and a substantially X-ray transparent animal restraint enclosure.

According to yet another aspect, the present invention provides a method of performing a CT scan on an animal patient in a CT scan apparatus having a patient target position, to produce CT scan image results of the animal patient. The method comprises placing the animal patient in substantially X-ray transparent animal restraint enclosure, placing the animal restraint enclosure in the patient target position for the CT scan, and conducting the CT scan.

In various embodiments, the CT scan is carried out according to CT scan protocols including about 80 to about 140 kV (kilovolts), about 50 to about 350 mA (milliAmperes), about 0.4 to about 2 second rotation speed(s), about 0.5 to about 10 mm (millimeter) slice thickness, and about 0.5 to about 10 mm slice reconstruction interval with a pitch of about 0.5 to about 2.

BRIEF DESCRIPTION OF THE DRAWINGS

FIG. 2b is an elevation end view of the base member FIG. 2a.

FIG. 3b is an elevation end view of the lid of FIG. 3a.

DETAILED DESCRIPTION

Figure 1:
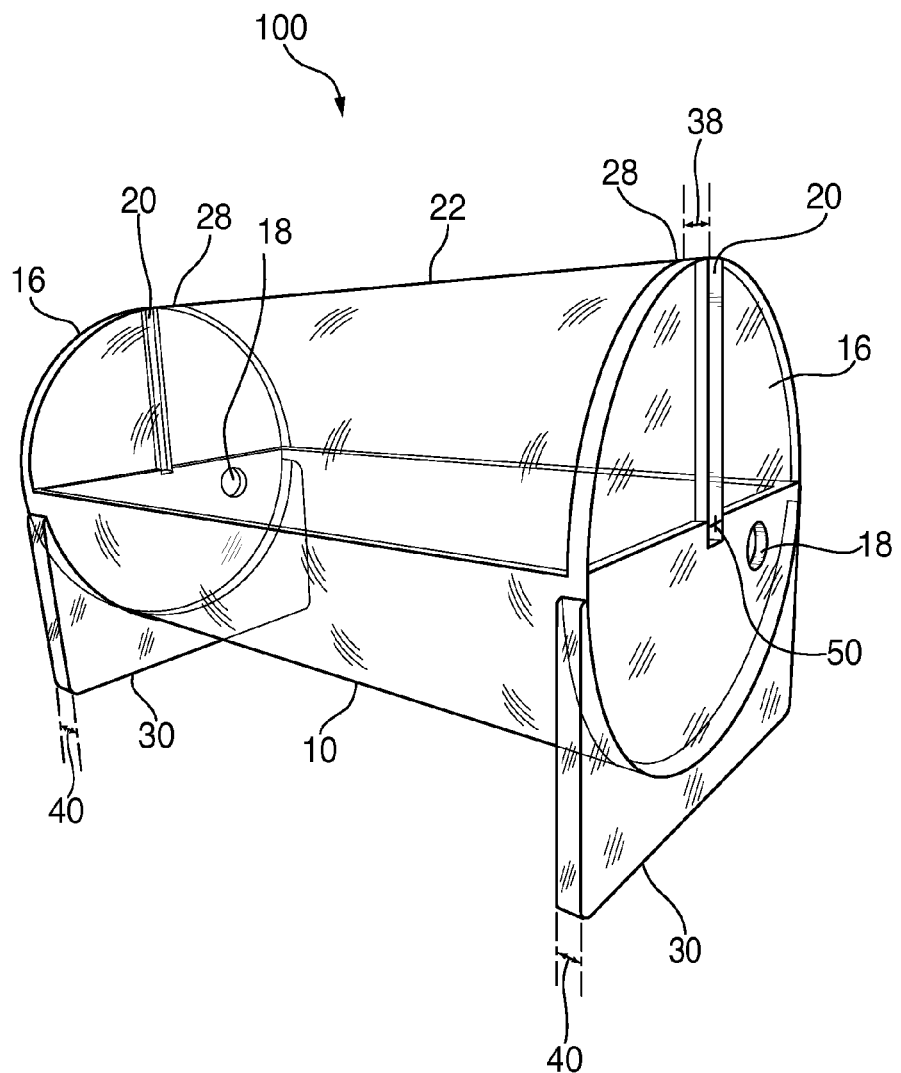
FIG. 1 is a perspective view of a particular embodiment of an animal restraint enclosure according to one aspect of the invention.
Figure 2A:
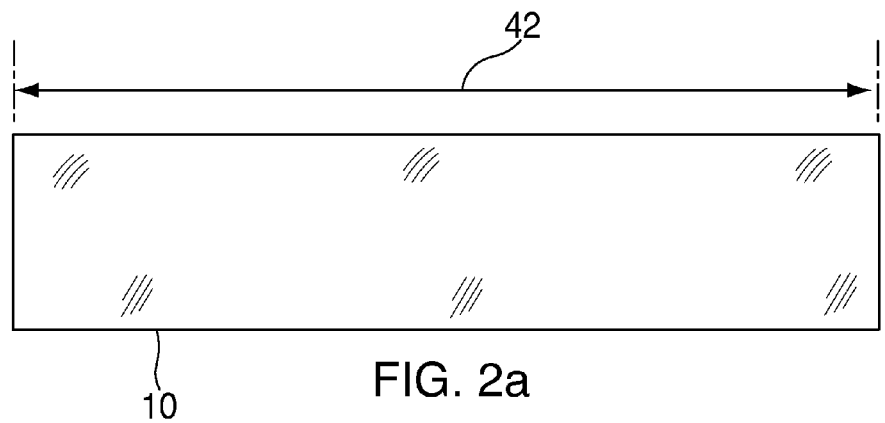
FIG. 2a is an elevation side view of the base member of the enclosure of FIG. 1.
Figure 2B:
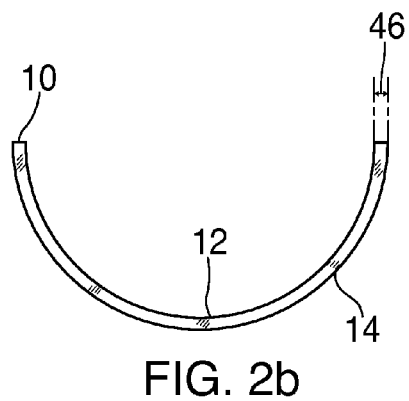
Figure 2C:
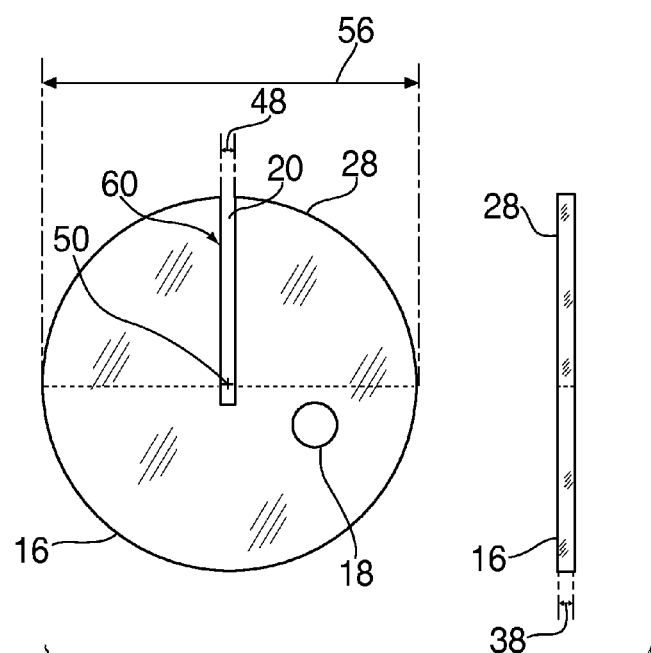
FIG. 2c is an elevation face view and side view of an end panel of the enclosure of FIG. 1.
Figure 3A:
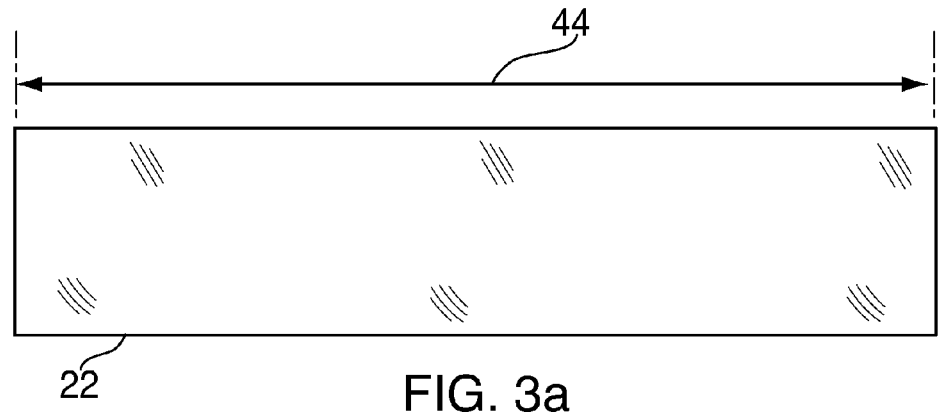
FIG. 3a is an elevation side view of the lid of the restraint enclosure of FIG. 1.
Figure 3B:
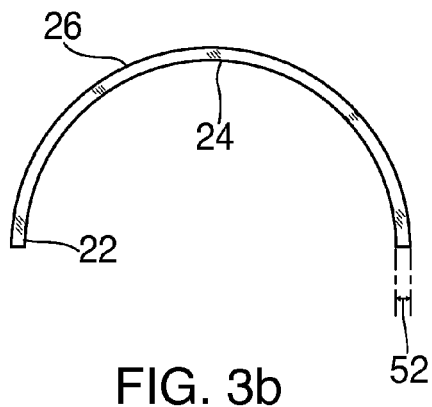
Figure 3C:
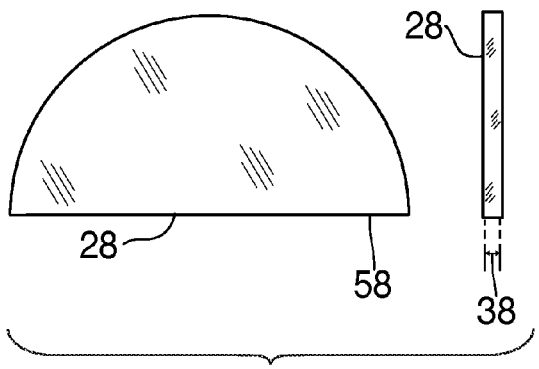
FIG. 3c is an elevation face view and side view of lid end of the enclosure of FIG. 1.
Figure 4:
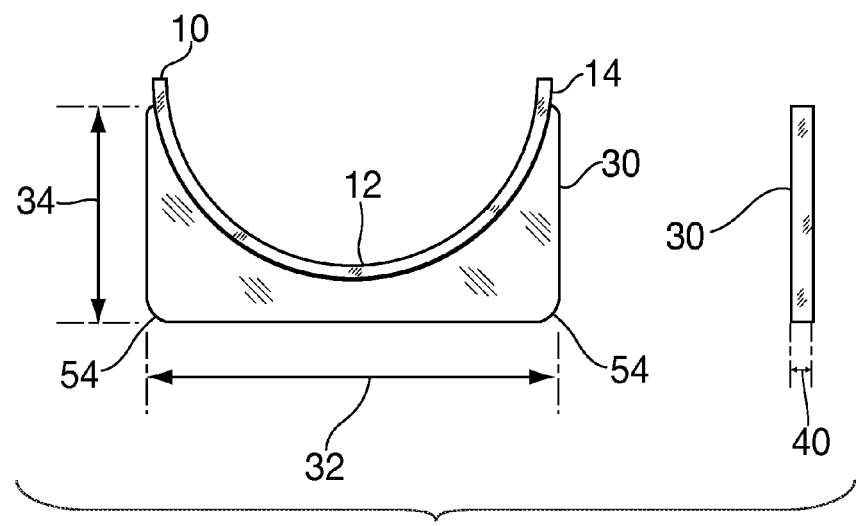
FIG. 4 is an elevation end view of the base member of FIG. 2a received on a saddle, and an elevation side view of the saddle.

In one embodiment, an animal restraint enclosure ("enclosure") indicated generally at 100 in FIG. 1 and now described with reference to FIG. 1-FIG. 4, is constructed from substantially X-ray transparent material. Such materials include thermoplastics such as polymethylmethacrylate, polycarbonate, polyacrylate, etc., optionally including carbon or other fibers for reinforcement. The overall size of the enclosure 100, as well as its strength (which the artisan of ordinary skill will understand to be determined in significant part by the choices of material, thickness and joint strength of the components of the enclosure) determine the types of animals for which the enclosure may be used. The enclosure 100 may be constructed from material that is visually transparent or translucent as well so that the animal patient can be observed while disposed therein. Visual transparency also allows the patient to see its surroundings from within the enclosure 100, thus likely reducing stress for the animal patient by reducing claustrophobic-type reactions to being restrained in the enclosure. The enclosure 100 is configured to stand stably on the surface of the patient platform of the CT scanner but is otherwise generally cylindrical and is sized to fit within the opening of a CT scanner gantry or target ring, although the invention is not limited in this regard and in other embodiments the enclosure may have other overall configurations.

The enclosure 100 includes two principal parts: a base structure and a removable lid. The base structure provides a receptacle which is configured to stand on the surface of the CT scanner platform and to receive the animal patient therein. As illustrated, the base structure includes a base member 10 having two ends, two end panels 16, and two saddles 30.

The base member 10 has two ends, a length 42, a thickness 46, and a semi-cylindrical configuration having a concave interior surface 12 and a convex exterior surface 14 which provides sides for the enclosure 100.

Each end panel 16 has a diameter 56 which corresponds to the diameter of the enclosure 100. The length 42 and diameter 56 may be selected to accommodate particular types of animals. For example, for cats, the length 42 may be about 40 centimeters (cm). The diameter 56 for CT imaging in cats may be about 20 to about 24 cm; whereas for imaging dogs the diameter 56 may be up to about 40 cm. Each end panel 16 has a thickness 38 and a narrow slot 20 which opens to the exposed edge (unnumbered) of the end panel. The slot 20 has a width 48 dimensioned to accommodate the passage of intravenous lines, one or more sensor leads, a leash or other necessary medical or animal handling accessory which must remain attached to the animal and which must reach outside the enclosure 100 during the CT scan. For example, the width 48 may be about 0.5 to about 1 cm. Optionally, the slot 20 extends from the exposed edge to beyond the center 50 of the end panel 16. In addition, at least one panel 16, optionally both end panels 16, has at least one aperture 18 formed therein for use as access port for fluid flow or instrumentation, as described further below. An end panel 16 is secured to each end of the base member 10 such that the slot 20 extends away from the base member.

Each saddle 30 has a flat bottom surface (unnumbered), a curved recess 36 on the top for receiving the base member 10, and a width 32, a height 34 and a thickness 40. The saddles 30 provide a footing for the base member 10 and are spaced apart from each other to enable the base member to stand stably on a flat surface such as a CT scanner patient table or a veterinary examining table. Each saddle has bottom corners 54 which are shaped to prevent chipping and cracking when being moved on or across a surface. Shaping of the bottom corners 54 can include rounding of the corners, as shown.

The enclosure 100 includes a lid 22 which is configured to cooperate with the base structure to define the compartment within which the animal patient will be restrained. In the illustrated embodiment, the lid 22 has a semi-cylindrical configuration with a length 44, a thickness 52, a concave interior surface 24 and a convex exterior surface 26. The lid 22 has two ends and includes a lid end 28 at each end. The lid 22 is dimensioned and configured like the base member 10. Optionally, the lid 22 and the base member 10 may be obtained by splitting a cylinder lengthwise into two halves. Accordingly, the diameter 58 of the lid 22 and lid end 28 matches the diameter of the base member 10 and the diameter 56 of the end panels 16, and the base structure and the lid have respective mating surfaces. When the lid 22 is placed on the base member 10, they cooperate to define a cylinder with a cylindrical space between them. In addition, each lid end 28 overlaps an end panel 16 and obstructs at least a portion, optionally a substantial portion, of the slot 20 so that with the lid 22 in place on the base member 10, the unobstructed portion of slot 20 provides a passage through the end of the enclosure 100. Optionally, the ends of the base member 10 and the lid 22 may be recessed to receive the end panels 16 within the outer circumference of the cylinder formed by the base member 10 and the lid 22.

The base member 10, end panels 16, saddles 30 can be secured together in any desired manner to form the base structure of the enclosure 100, preferably without the use of X-ray visible materials. For example, when the base member 10, end panels 16, saddles 30 are all formed from polymeric materials, they may be joined by mechanical, chemical, or thermal means, many of which are known in the art. The base structure and lid 22 are configured so that the lid can easily be removed from and replaced on the base structure, however the invention is not limited in this regard and in other embodiments, the lid may optionally be mounted on the base structure by a hinge. While the apertures 18 and slot 20 are formed in end panels 16 in the illustrated enclosure 100, this is not a limitation on the invention and in other embodiments, these features may be provided elsewhere in the enclosure, e.g., elsewhere on the base member 10 or on the lid 22.

In use, the lid 22 is removed from the base structure and the animal patient (e.g., a cat), which may optionally be alert (i.e., non-sedated or non-anesthetized) is placed in the base member 10. Any I-V lines, sensor leads, etc. that are connected to the animal patient are inserted into a slot 20. If needed, one or more gas lines (e.g., gas flow lines such as a fresh air or an oxygen line and an exhaust line) are coupled to, or are passed through, the apertures 18. The enclosure and the animal patient therein are placed on the table of the CT scanner in proper position for the scan (in the "patent target" position) relative to the CT scanner gantry or target ring, and the scan protocol is carried out. The animal patient may be unrestrained within the enclosure. Since no personnel are needed to restrain the animal in the target position for the protocol, the personnel may exit the room during the protocol and thus reduce their own incidental exposure to radiation. When the scan protocol is complete, the lid 22 is removed and the animal patient can be withdrawn from the enclosure 100.

The use of the enclosure 100 in a clinical situation when using only one protocol results in a total time in the CT scanner when scanning non-sedated animal patients that is significantly reduced in comparison with a protocol not using the enclosure. When the apparatus is coupled with a 16-slice CT scanner it provides whole-body images of animals to be successfully acquired in a very short period of time with excellent spatial resolution in all three planes and with negligible motion artifact. Use of the enclosure 100 also obviates the need for direct manipulation of animal patients and results in a less stressful environment for the animal patients in comparison with a protocol not using the enclosure. The enclosure 100 also allows effective oxygen and catheter-based therapy for animals with respiratory compromise while maintain temperature and $CO_2$ at safe levels that allows for optimized CT imaging of unsedated, unanesthetized animals.

The enclosure 100 may be used with a conventional CT scan protocol, or with a protocol as described herein.

In various embodiments, an enclosure as described herein meets one or more of the following clinical needs: 1) allow access for oxygen administration at therapeutic levels; 2) allow access for intravenous lines without the need to disconnect the lines when placing or removing the 85 patients from the apparatus; 3) be symmetric, providing ports for catheter and oxygen access on both ends of the apparatus; 4) be transparent, allowing visual observation of the patient; 5) have a closure mechanism that allowed quick removal of the patient; 6) have a secure closure mechanism preventing patient escape; 7) provide a low heat and carbon dioxide environment; 8) avoid clinically relevant elevation of carbon dioxide; 9) be portable; and 10) be easily disinfected. In addition, the invention meets one or more of the following imaging needs: 1) have low x-ray attenuation, 2) have a symmetric, curved cross-sectional shape to avoid imaging artifacts, 3) have a narrow and short lumen to limit patient motion, 4) have no metal parts, 5) be rugged enough for daily use, and 6) allow additional padding to compensate for patients of different body size and behavioral characteristics.

As described herein, the invention provides a low-attenuating (i.e., substantially X-ray transparent), optionally visually transparent enclosure 100 that also functions as a clinically supportive environment that allows for comparison of protocols for CT of the thorax in awake cats inside the enclosure. The enclosure 100 allows cats and other suitable mammals to be imaged without direct manipulation, and the CT examination is much less stressful than thoracic radiographs because there is minimal stress of restraint and no stress of positioning. As described in the Example below, computed tomographic examinations were successfully performed in 20 of 22 cats when placed inside the enclosure 100. The cats tolerated the enclosure 100 very well and remained still for almost the entire CT examination.

Example 1

Phase 1 Test

In ten separate trials, ten clinically healthy young adult cats ranging in size from 3.3 to 7 kg (kilograms) (mean 4.9 kg) were placed inside an enclosure 100 and the following parameters were measured at times 0, 5, 10, 15, 20, 25 and 30 minutes using an anesthesia monitor: carbon dioxide ($CO_2$), fraction of inspired oxygen ($FiO_2$), internal chamber temperature and subject respiratory rates. The tubing that would normally fit onto a special cuff on the endotracheal tube was inserted into the enclosure 100 through one of the apertures 18. The anesthesia monitor recorded end tidal $CO_2$ ($ETCO_2$), which was extrapolated as the carbon dioxide level within the apparatus. The $FiO_2$ was measured via the same tubing. A probe to measure temperature was placed into another aperture 18 of the enclosure. Oxygen was provided via an oxygen flow meter, with humidifier, at a rate of 2 liters/minute (1/min) into an oxygen port on the other end of the apparatus. Cats were not restrained inside the enclosure 100, i.e., they were free to move within the enclosure.

Each cat was placed inside the enclosure as described herein prior to the CT examination. The base member and lid were configured to define a transparent acrylic tube with a wall thickness of 5 mm, outer diameter of 21 cm (centimeters), and length of 40 cm. The mutually engaging surfaces were not sealed, which allowed excess gas to escape, and prevented pressure, heat and humidity accumulation. The cats were monitored visually throughout the imaging procedure and removed quickly in case of an emergency. Oxygen and catheter line access was achieved by disposing the lines into the slot. After closure with placement of the lid, the slot was reduced to a 6 mm (millimeter)×6 mm passage. The enclosure had low attenuation (approximately 54 Hounsfield units) and did not cause visible artifacts during CT image acquisition.

End tidal carbon dioxide, $FiO_2$, temperature inside the apparatus, and respirator rates of the cats are presented in Tables 1 and 2. End tidal carbon dioxide is defined as the partial pressure or maximal concentration of carbon dioxide ($CO_2$) at the end of an exhaled breath, which is expressed as a percentage of ($CO_2$) or mmHg. During the measurements, one cat was active after being placed in the apparatus and kept moving during the 30 minute interval. The other 9 cats remained quiet most of the time, with no overt signs of stress.

TABLE 1

$CO_2$ and $FiO_2$ Measurements Inside the Enclosure

| | $CO_2$ (mmHg) | | | $FiO_2$ (%) | | |
|---|---|---|---|---|---|---|
| Time (min) | Mean | SD | Min-Max | Mean | SD | Min-Max |
| 0 | 0* | 0-5† | 0-6 | 20.7* | 20-30† | 20-33 |
| 5 | 10.5 | 4.1 | 6-19 | 53.2 | 17.1 | 30-85 |
| 10 | 10.1 | 4.1 | 3-16 | 64.2 | 14.2 | 44-85 |
| 15 | 11.1 | 3.9 | 7-17 | 66.8 | 17.7 | 36-93 |
| 20 | 11.5 | 4.9 | 3-17 | 61.1 | 20.4 | 32-95 |
| 25 | 9.2 | 4.1 | 5-18 | 68.1 | 19.5 | 40-95 |
| 30 | 9.7 | 4 | 4-18 | 65.9 | 15.6 | 42-86 |

*Median.
†80% Percentile.
$CO_2$ carbon dioxide, measured as end-tidal carbon dioxide; $FiO_2$, fraction of inspired oxygen, $FiO_2$ at room air = 21%;
SD, standard deviation; Min-Max, minimum-maximum.

TABLE 2

Temperature Inside the enclosure and Respiratory Rate of Cats

| | Temperature (° C.) | | | RR (bpm)* | | |
|---|---|---|---|---|---|---|
| Time (min) | Mean | SD | Min-Max | Mean | SD | Min-Max |
| 0 | 23.5 | 0.9 | 22-24 | 52.9 | 14.8 | 24-72 |
| 5 | 25.4 | 1.5 | 23-27 | 51.3 | 13.8 | 30-66 |
| 10 | 25.9 | 1.2 | 24-28 | 47.6 | 14.3 | 28-66 |
| 15 | 26.1 | 1.1 | 25-28 | 50.7 | 18.5 | 28-80 |
| 20 | 26.4 | 1 | 25-29 | 47.3 | 15.8 | 28-66 |
| 25 | 26.7 | 1 | 25-29 | 47.3 | 14.6 | 28-66 |
| 30 | 26.8 | 1 | 26-29 | 46.9 | 14.7 | 28-68 |

*RR respiratory rate in beats per minute. Recorded in nine cats.
SD, standard deviation; Min-Max, minimum-maximum.

There was a statistically significant difference in $ETCO_2$ levels at time 0 compared to times 5-30 minutes; however, there was no difference in $ETCO_2$ levels over time after 5 minutes. The maximum $CO_2$ level inside the apparatus at all times was 19 mmHg. There was a significant difference of ($FiO_2$) levels at time 0 compared to times 5-30 minutes with the levels increasing over time.

There was a significant difference in $FiO_2$ levels comparing 265 measurements at 5 minutes to 10, 15 and 25 minutes. No difference was found comparing measurements at 5 minutes to 20 or 30 minutes.

Similarly a significant difference in temperature was found at time 0 compared to times 5-30 minutes, with the temperature increasing over time. The highest measurement, of 29° C., was found at 20, 25 and 30 min. Respiratory rate was recorded in 9 of the 10 cats, and no difference was found over time. Mean respiratory rate at time 0 was 53 breaths per minute (bpm), while at time 30 minutes it was 47 bpm.

Based on physiologic measurements, the apparatus has been determined to be safe and well tolerated by the cats. The difference between $ETCO_2$ levels at time 0 compared to times 5-30 min was expected since initially no cat was inside the apparatus and therefore the levels of $ETCO_2$ for all but one cat, were 0 mmHg. There was no statistical significant difference in $ETCO_2$ levels over time after 5 minutes, indicating that the levels of $CO_2$ inside the apparatus do not increase for up to a period of 30 minutes. Although not statistically significant, decreasing $CO_2$ levels were found at the maximum times (25 and 30 min.) compared to initial times. The maximum $CO_2$ level inside the apparatus at any time was 19 mmHg.

The significant difference of $FiO_2$ levels found at time 0 compared to times 5-30 minutes with increasing levels of oxygen up to 25 minutes indicates the apparatus works properly as an oxygen provider. An oxygen flow rate of 2 L/min provided a mean $FiO_2$ inside the apparatus of 53% at 5 minutes and 68% at 25 minutes with a maximum of 95% $FiO_2$ ($FiO_2$ at room air=21%).

There was a significant difference of temperature levels inside the apparatus over time with the highest mean of 26.8° C. at 30 minutes. Overall, the mean temperature was within a narrow and safe range of 23.5° C. to 26.8° C. There was no significant change in respiratory rate of the cats indicating that the temperature and $CO_2$ rise were not significant to cause any increase in respiratory rate and effort. This is most important for cats in respiratory distress as the apparatus should not contribute to increased respiratory rate or effort.

Respiratory rate was recorded in 9 of 10 cats and no statistical significant difference was found over time. Mean respiratory rate at time 0 was 53 breaths per minute (bpm) and at time 30 minutes it was 47 bpm. These values are mildly above the normal (20-44 bpm), possibly indicating some degree of stress. However the fact that they were higher at 0 minutes compared to any other time could indicate that the cats were stressed by other reasons such as being in the hospital and being handled, rather than by the apparatus itself. After 20 minutes inside the apparatus the respiratory rates began to decrease and achieved the lowest mean at the maximum time (30 minutes).

Example 2

Phase 2 Test

Twenty-two clinically healthy cats were each imaged within the enclosure 100. Demographic and morphologic parameters of the cats are shown in Table 3.

TABLE 3

Data Distribution of Phase 2 Cats

|  | Mean | SD | 95% CI | Min-Max |
|---|---|---|---|---|
| Age (years) | 7.5 | 4.5 | 5.4-9.7 | 1-15 |
| BW (kg) | 4.6 | 2 | 4.2-5.1 | 3-6.1 |
| WC (cm) | 12.8 | 2.7 | 11.6-14 | 8.4-17.5 |
| HC (cm) | 14.3 | 1.4 | 13.7-15 | 11.9-16.5 |
| Total time at CT (min) | 12.7 | 6 | 9.9-15.6 | 5-28 |

BW, body weight;
WC, width of chest;
HC, height of chest;
SD, standard deviation;
CI, confidence interval;
Min-Max, minimum-maximum.

The mean age of the cats was 7.5 years and the mean body weight 4.5 Kg. There was no statistical significant difference between randomized versus non-randomized cats and the statistical analysis was performed adding these 2 groups. The mean total time at CT was 12.5 minutes, with a range of 5-28 minutes. With the exception of 5 cats, the total time at CT was below 15 minutes.

The twenty-two awake, non-sedated normal cats were imaged without contrast medium using a 16 slice helical CT unit to evaluate dose equivalent protocols. Two different x-ray tube potentials (kV's), 80 and 120, and 2 different helical pitches, 0.562 and 1.75, were evaluated. The signal intensity of the pulmonary parenchyma (SIlung), signal intensity of background (SIbackgr.), contrast, noise, signal-to-noise ratio (SNR) and contrast-to-noise ratio (CNR) were calculated. Three evaluators ranked the images for sharpness of liver margins, motion, helical, and windmill artifacts. Computed tomography was successfully completed in 20 of 22 cats. No artifacts directly related to the enclosure were detected. Overall, 75 of 80 (94%) successfully completed examinations were judged to have absent or minimal motion artifact.

The results for the quantitative evaluation are displayed in Table 4.

TABLE 4

Quantitative Results

| | Protocol 1 | | Protocol 2 | | Protocol 3 | | Protocol 4 | |
|---|---|---|---|---|---|---|---|---|
| | Mean | SD | Mean | SD | Mean | SD | Mean | SD |
| $SI_{lung}$ | −827.8[a] | 53.5 | −831.2[a] | 59.2 | −814.3[a] | 56.2 | −822.6[a] | 59 |
| $SI_{backgr}$ | 61.9[a] | 3.2 | 62.4[a] | 4.9 | 60.4[ab] | 2.5 | 58.7[b] | 5.4 |
| Contrast | 765.9[a] | 53.2 | 768.8[a] | 58.5 | 753.9[a] | 57.4 | 763.9[a] | 61.4 |
| Noise | 20.4 | 0.09 | 17.8 | 0.2 | 18.5 | 0.2 | 16.3 | 0.1 |
| SNR | 40.5[a] | 2.6 | 46.7[b] | 3.2 | 44[c] | 3 | 50.6[d] | 3.5 |
| CNR | 37.5[a] | 2.6 | 43.2[b] | 3.3 | 40.7[c] | 3.1 | 47[d] | 3.8 |

Within a row, protocols with like letter superscripts are not statistically significantly different from each other.

$SI_{lung}$ = signal intensity in the lung; $SI_{backgr}$ = signal intensity in the background; SNR = signal-to-noise ratio; CNR = contrast-to-noise ratio.

A statistically significant difference was found for SNR and CNR between all protocols. Among the same kV, protocols with the higher pitch had had significantly lower noise and the highest SNR and CNR, and among the same pitch, protocols with higher kV had the highest SNR and CNR. The contrast was higher in protocols with lower kV although the difference was not statistically significant. There was no statistically significant difference for SIlung between any protocols. The results for noise and CTDIvol were similar for all 4 protocols (see Table 5).

TABLE 5

Pearson's Correlation Coefficient of Quantitative Variables

|  | $SI_{Lung}$ | $SI_{Backgr}$ | Noise | SNR | CNR |
|---|---|---|---|---|---|
| Protocols | 0.06* | −0.3 | −0.5 | 0.4 | 0.3 |
| Age (years) | −0.4 | −0.25* | −0.22* | 0.3 | 0.3 |
| BW (kg) | 0.37* | 0.5 | 0.3 | −0.43* | −0.4 |
| WC (cm) | 0.4 | 0.07* | 0.3 | −0.4 | −0.4 |
| HC (cm) | −0.14* | 0.16* | −0.01* | 0.06 | 0.06* |

*Not statistically significant.
$SI_{Lung}$, signal intensity in the lung;
$SI_{Backgr}$, signal intensity in the background;
SNR, signal-to-noise ratio;
CNR, contrast-to-noise ratio.

There was a statistically significant although weak positive correlation of body weight with SIbackg and noise, and negative correlation with CNR. Similarly, width of the thorax had a weak positive correlation with SIlung and noise, and negative correlation with CNR and SNR. Age had a significantly although weak positive correlation with SNR and CNR, and negative with SIlung. The height of the thorax was not correlated with any of the parameters.

Qualitative results are summarized in Tables 6-8.

TABLE 6

κ Statistic Interobserver Agreement

| Evaluator* | Liver Margins | Helical Artifact | Windmill Artifact |
|---|---|---|---|
| A-B | 0.59 | 0.72 | 0.9 |
| A-C | 0.7 | 0.72 | 0.75 |
| B-C | 0.72 | 0.74 | 0.8 |

*Evaluator A and C: board-certified radiologists; evaluator B: certified CT technician. <0 less than chance agreement; 0.01-0.20 slight agreement; 0.21-0.40 fair agreement; 0.41-0.60 moderate agreement; 0.61-0.80 substantial agreement; 0.81-0.99 almost perfect agreement.

TABLE 7

Percentage of Slices Affected by Motion Artifact

| Protocol | 1 | 2 | 3 | 4 |
|---|---|---|---|---|
| Cats |  |  |  |  |
| 1 | 3% (8/241) | 0% | 9% (23/243) | 0% |
| 6 | 10% (25/243) | 0% | 15% (35/230) | 0% |
| 8 | 10% (17/174) | 0% | 0% | 0% |
| 9 | 7% (15/216) | 0% | 0% | 0% |
| 10 | 7% (16/229) | 0% | 6% (13/233) | 0% |
| 11 | 0% | 0% | 9% (21/243) | 0% |
| 12 | 0% | 0% | 10% (21/206) | 0% |
| 13 | 9% (19/207) | 0% | 8% (16/198) | 0% |
| 14 | 0% | 0% | 8% (17/202) | 0% |
| 15 | 0% | 4% (6/162) | 0% | 0% |
| 16 | 6% (11/185) | 0% | 4% (7/175) | 0% |
| 17 | 6% (11/198) | 19% (37/199) | 0% | 7% (14/198) |
| 20 | 0% | 0% | 9% (18/192) | 0% |

Cats 2, 3, 4, 5, 7, 18, and 19 had no images affected by motion

TABLE 8

Number of Times Each Score Appeared Combining All Three Evaluators

| | Protocol | | | | | | | | | | | |
|---|---|---|---|---|---|---|---|---|---|---|---|---|
| | Liver Margins | | | | Helical Artifact | | | | Windmill Artifact | | | |
| Score | 1 | 2 | 3 | 4 | 1 | 2 | 3 | 4 | 1 | 2 | 3 | 4 |
| 0 | $5^a$ | $49^b$ | $4^a$ | $53^b$ | $47^a$ | $2^b$ | $50^a$ | $3^b$ | $57^a$ | $1^b$ | $53^a$ | $3^b$ |
| 1 | $55^a$ | $11^b$ | $56^a$ | $7^b$ | $13^a$ | $58^b$ | $10^a$ | $57^b$ | $3^a$ | $59^b$ | $7^a$ | $57^b$ |

Within a row, protocols with different letters show statistically significant difference.
Liver margins: sharp-0, blurred-1; helical artifact: absent-0, present-1; windmill artifact: absent-0, present-1.
Protocols with different superscript letters a and b show statistically significant difference from each other The data above shows that interobserver agreement was moderate to substantial for evaluation of liver margins, substantial for helical artifact and substantial to almost perfect for windmill artifacts. For overall motion, protocols with high pitch had significantly less motion artifact compared with protocols using low pitch. For location of motion artifact, there was no statistical difference based on the reader's score for any protocol in any location. Overall, 75 out of 80 (94%) examinations were judged to have absent or minimal motion artifact.

There was a statistically significant difference for windmill and helical artifacts between protocols with 1.75 and 0.562 pitch, with 0.562 pitch protocols having less windmill and helical artifacts. There was also a significant difference for liver margins between protocols with different pitch, with higher pitches showing sharper liver margins than lower pitches.

Each cat was place in an enclosure, and the enclosure was secured to the CT table with standard CT table Velcro-type hook-and-loop fastener straps. These straps also provided additional security to the lid of the enclosure. Supplemental foam wedges were added as necessary to encourage the cats to remain in a neutral sternal position within the enclosure. Cats were not restrained inside the enclosure and were monitored visually throughout the procedure. Oxygen was provided at a flow of 2 liters/min for all animals during the procedure. To avoid pre-scan scouts, images were acquired of the entire enclosure, which resulted in a whole-body study. The CT table was kept at a pre-determined height of 170 cm, and the enclosure was always placed on a same pre-determined position on the CT table. Post-image acquisition, the cats were removed from the enclosure.

Two cats exhibited signs of overstress inside the enclosure and were excluded from the study. In 20 out of 22 cats CT was completed without complications. Two cats had signs of overt stress and attempted to escape from the enclosure. The first attempt to image one of these cats resulted in extreme motion artifact; the CT examination was terminated. The second cat remained in dorsal recumbency and was pushing the top of the apparatus with all four limbs and CT examination was not attempted. These two cats were excluded from the study. The remaining 20 cats had no signs of physical or respiratory distress and remained in a sternal resting position for almost the entire CT examination. Some cats moved their head from side to side and some would flip 180° inside the apparatus and then remain still. Approximately 50% of cats had at least one protocol repeated due to motion artifact. The images were acquired from cranial to caudal in most cats. Most original transverse plane images were characterized by mild to moderate obliquity before on-line manipulation. Presumed pulmonary atelectasis was present in one cat and seen in all protocols for this cat. This appeared as a small region of patchy alveolar pattern in a dependent region of the lung.

In the remaining 20 cats, two different kV settings (a low and a high kV (80 kV and 120 kV)) and two different helical pitch settings (0.562 and 1.75) were tested while keeping the CT dose index (CTDIvol) of the scans constant, resulting in four dose equivalent protocols. The CT protocols are displayed in Table 9.

TABLE 9

Computed Tomography (CT) Protocols

| | Protocol 1 | Protocol 2 | Protocol 3 | Protocol 4 |
|---|---|---|---|---|
| Tube voltage (kV) | 80 | 80 | 120 | 120 |
| Pitch | 0.562 | 1.75 | 0.562 | 1.75 |
| Tube Current (mA) | 130 | 400 | 45 | 145 |
| mA | 65 | 200 | 22.5 | 72.5 |
| Effective mA | 116 | 114 | 40 | 41 |
| Rotation time (s) | 0.5 | 0.5 | 0.5 | 0.5 |
| Field of view (cm) | 25 | 25 | 25 | 25 |
| Slice thickness (mm) | 1.25 | 1.25 | 1.25 | 1.25 |
| Increment (mm) | 0.625 | 0.625 | 0.625 | 0.625 |
| Total scan time (s) | 36.7 | 11.9 | 36.7 | 11.9 |
| $CTDI_{vol}$ (mGy) | 8.71 | 9.39 | 8.36 | 8.66 |

$CTDI_{vol}$, volumn CT dose index.

The scan rotation time for all imaging in this study was 0.5 seconds. The initial protocol was set as 80 kV, a pitch of 1.75 and 400 mA. To get a protocol with the same kV and a pitch of 0.562, the mA was decreased by the same factor that the pitch was decreased (0.32), resulting in 128 mA. Thus both protocols had the same effective mAs (mA×rotation time/pitch) of 114. To change the kV, information from the technical data sheet of the CT scanner was used. According to the data sheet provided with the CT scanner, to change the kV from 80 kV to 120 kV while keeping the CTDIvol constant, the mA needed to be decreased by multiplying by a factor of 0.36. The next protocols were: 120 kV, a pitch of 1.75, and 144 mA (400×0.36) and 120 kV, a pitch of 0.562, and 46 mA (128×0.36). This CT scanner only allowed mA settings in increments of 5 and so automatically changed the previous mA settings as follows: 128 to 130, 144 to 145 and 46 to 45.

A detector configuration of 16×0.625 mm and beam collimation of 10 mm were used along with a "small" scan field of view. The image reconstruction parameters were: a display field of view of 25 cm, a 1.25 mm slice thickness, a 0.625 mm slice reconstruction interval. A moderately sharp ("detail") algorithm was used, which is somewhat sharper than smooth or standard algorithms, but less sharp compared to "bone" algorithms. This algorithm was chosen to deliver the best compromise between resolution and image noise. The protocols were repeated if severe motion artifact was detected by subjective evaluation during the scan. The original scanned images were manipulated on a separate workstation to obtain symmetric transverse plane images of the thorax. Subsequent multiplanar reformatting was performed to obtain dorsal and sagittal images, reconstructed with a 0.625 mm slice thickness and a 0.312 mm slice reconstruction interval.

The CT protocols were non-randomized for the first 10 and randomized for the second 10 cats. The data from randomized and non-randomized cats were evaluated for statistical significant differences.

For each protocol, total scan time and radiation dose measurements were recorded, the latter based on the scanner-generated CT dose index volume values (CTDIvol) for a 16 cm phantom. The total time spent on CT was recorded for each cat from the time the cat entered the CT room until the time the cat left the CT room. Cats were removed from the enclosure immediately after leaving the CT room. Quantitative image analysis was performed using a GE Advantage Workstation. All measurements were made on the original 1.25 mm thickness transverse images by one author (CRO). Signal intensity of the pulmonary parenchyma (SIlung) was defined as the attenuation (CT numbers in Hounsfield units) measured by placing a circular region of interest (ROI) in the dorsal pulmonary parenchyma at the level of the caudal thorax. The ROI size was 22 mm 2, the largest possible that could be drawn while avoiding the inclusion of bronchi and vessels.

Signal intensity of background (SIbackgr.) was defined as the attenuation measured by placing a circular ROI in the paraspinal muscle at the level of the caudal thorax. The ROI size was 45 mm2, the largest possible that could be drawn while avoiding the inclusion of adjacent bones. To minimize bias from a single measurement for both SIlung and SIbackgr, the measurements were made at 5 different locations in 5 subsequent images and the mean value was used for further calculations.

Contrast was calculated as SIlung−SIbackgr. The background noise was calculated on a phantom. The phantom was a round plastic container measuring 14.5 cm in diameter (approximately the diameter of the chest in a cat) and with a 2.0 mm wall thickness that was filled with water. Regions of interest of 400 cm2 were placed in the center of the phantom in 5 subsequent images for each protocol. Averaged numbers were used for further calculations.

Signal-to-noise ratio (SNR) was calculated by dividing the mean CT number of the lung by the background noise (SIlung/noise). Contrast-to-noise ratio (CNR) was calculated as follows:

$$CNR = (SIlung - SIbackgr.)/noise.$$

The lateral and dorsoventral diameter of the thorax were measured for each cat at the level of the widest dimension of the thoracic cavity by placing the cursor on the edge of the skin. For cats aligned with the limbs in contact with the chest, the limbs were included in the measurements.

All images were initially evaluated qualitatively by one reviewer. The CT protocols were hidden from each image. During this first review, any artifacts encountered were recorded. These included blurred liver margins, helical, motion and windmill artifacts. Windmill artifact consists of black/white patterns that spin off of high contrast features that vary along the longitudinal (z-) axis. When the images are viewed in cine mode, the artifact appears to spin like a windmill. In dorsal or sagittal images, they appear as bands. The helical artifact appeared as large areas in the lung with no attenuation. Helical artifact, like windmill, is related to the need for data interpolation in helical scanning, which can result in areas of artificially high or low CT numbers near regions of large CT number changes.

For subsequent analysis, all data sets were evaluated by 2 board certified radiologists and one certified CT technician. Images were randomized and displayed in transverse plane in lung window (window level=−500, window width=1500). Readings were performed independently for liver margins, windmill and helical artifact, and in consensus for motion artifact; evaluators were not aware of CT acquisition parameters for any image. A standardized questionnaire was used for image evaluation as follows: 1) liver margins: sharp—0, blurred—1; 2) helical artifact: absent—0, present—1; 3) windmill artifact: absent—0, present—1; 4) motion artifact: absent—0, minimal—1, moderate—2, severe—3.

Motion artifact was ranked according to the following locations: cranial thorax, if the motion artifact appeared predominantly cranial to the heart but not including the heart;

middle thorax, if the motion appeared predominantly cranial to liver but not including the liver; and caudal thorax, if the motion appeared predominantly from where the liver begins until the end of the thorax. Images were assigned the most severe score. The overall score for motion artifact for each cat was considered the highest score among the locations. For each protocol, the percentage of slices affected by motion was calculated for each cat in which motion was found. Finally, for liver margins, helical, and windmill artifacts the number of times each score appeared combining all three evaluators was calculated and compared among each protocol.

The Kolmogorov-Smirnov test was used to evaluate the distribution of the data. Normally distributed data were reported by mean, standard deviation (SD), and minimum-maximum values, while non-normally distributed data were reported by median, 10-90% and minimum-maximum values. A 2-way ANOVA test was used to compare the protocols between the randomized versus non-randomized cats for SI (muscle and lung), noise, contrast, SNR and CNR. For ETCO2, FiO2, temperature, and respiratory rate, non-normally distributed data were analyzed using Friedman's test, while a repeated measures general linear model was performed for normally distributed data. Post-hoc tests were used to compare differences to time 0 when significant. A one-way ANOVA test was performed to compare the protocols for SI (muscle and lung), noise, contrast, SNR and CNR data. Regression analysis was used to compare the different outcomes (SI in muscle and lung, noise, contrast, SNR and CNR) with the variables protocol, age, weight, width and height of thoracic cavity, and total time at CT. Differences in the protocols between the evaluators were compared using the chi-square test for homogeneity. When one box was less than 5, the Fisher exact test was used. For liver, helical, and windmill artifacts, Cohen's Kappa was used to assess the level of agreement between evaluators. Cohen's kappa coefficient is a statistical measure of inter-rater agreement or inter-annotator agreement for qualitative (categorical) items. A Fisher exact test was used to compare each protocol for liver, helical and windmill artifacts. A Kruskal Wallis test was used for the comparison of protocols for overall motion and to compare motion among the 3 different locations in the chest. Since a difference was found for overall motion among the protocols, a Mann-Whitney test was used to compare each protocol. A $P<0.05$ was considered statistically significant.

Example 3

Clinical Study in Feline Patients

Fifty-four cats presenting to a veterinary emergency department with a recent history of, or current clinical signs of, respiratory disease were stabilized and underwent CT thoracic imaging in an animal restraint enclosure as described herein without sedation or general anesthesia. Cats were typically placed in the enclosure while in the emergency room and transported to the radiology department. During transportation and CT scanning, oxygen was provided to dyspneic cats (41) at a flow of 2 liters/minute (1/min) through a tubing in the device at the cranial end of the patient. Images of the entire enclosure were acquired resulting in whole-body scanning in all cats. The CT protocol was: 0.562 pitch, either 80 kV and 130 mA, or 120 kV and 45 mA, collimation of 16" 0.625 mm, gantry rotation speed of 0.5 s, 25 cm field of view, 1.25 mm slice thickness with 0.63 mm increment and detail algorithm.

The CT examination was repeated once for each of seven cats because excessive motion by those cats during the initial examination resulted in a nondiagnostic imaging results. The nondiagnostic images were not included in the study. Intravenous iodinated contrast medium was administered as clinically indicated. Two of the cats had no precontrast CT imaging. In addition, thoracic radiographs were made in left and right lateral and either dorsoventral or ventrodorsal recumbency. Forty-one cats had a final diagnoses based on echocardiography, cytology, histopathology, necropsy, or clinical response to specific therapy. Follow-up was obtained when possible. In the remaining 13 cats a presumed diagnosis was made based on response to therapy and follow-up. The cats were separated into eight clinical classifications based on final diagnosis: (1), pulmonary neoplasia (2), lower airway disease, (3) cardiomyopathy (4) mediastinal mass (5) infection, (6) trauma, (7) hernia, and (8) other.

Of the 54 cats undergoing CT imaging, 50 also had radiography performed, of which 46 had complete three-view radiographic studies performed within 24 hours of CT imaging. Only these 46 cats were included in the statistical analysis for comparison between the imaging modalities, but all cats were evaluated for additional information and correct diagnosis provided by either imaging modality, image quality of the radiographic and CT studies, and time from presentation in the hospital to performing each study.

Results

The following Table 10 provides a comparison of accuracy in disease groups between computed tomography (CT) and radiography (Rad), showing the number of correct diagnoses based on imaging relative to the number of final diagnoses (N).

TABLE 10

Disease Groups and Comparison of Modalities

| Groups | N (number of cats) | CT gave Correct Diagnosis[1] | Number of cats with contrast medium for CT | Rad gave Correct Diagnosis | CT Additional Information | Rad Additional Information |
| --- | --- | --- | --- | --- | --- | --- |
| Lung neoplasia | 9 | 8/9 (88.9%) | 6 | 8/9 (88.9%) | 7/9 (77.8%) | 0/9 (0%) |
| Lower airway | 9 | 8/9 (88.9%) | 1 | 4/8* (50%) | 8/8* (100%) | 0/8* (0%) |
| Cardiomyopathy | 9 | 8/9 (88.9%) | 2 | 6/8* (75%) | 3/8* (37.5%) | 2/8* (25%) |
| Cranial Mediastinal mass | 8 | 8/8 (100%) | 4 | 6/7* (85.7%) | 6/7* (85.7%) | 1/7* (33.3%) |
| Pulmonary Infection | 7 | 2/7 (28.6%) | 3 | 1/7 (14.3%) | 5/7 (71.4%) | 0/7 (0%) |
| Trauma | 4 | 3/4 (75%) | | 0/4 (0%) | 4/4 (100%) | 0/4 (0%) |

TABLE 10-continued

Disease Groups and Comparison of Modalities

| Groups | N (number of cats) | CT gave Correct Diagnosis[1] | Number of cats with contrast medium for CT | Rad gave Correct Diagnosis | CT Additional Information | Rad Additional Information |
|---|---|---|---|---|---|---|
| Hernia | 3 | 2/3 (66.7%) | 2 | 1/2* (50%) | 1/2* (50%) | 0/2* (0%) |
| Miscellaneous | 5 | 3/5 (60%) |  | 3/5 (60%) | 3/5 (60%) | 0/5 (0%) |
| Total | 54 | 42/54 (77.8%) |  | 29/50 (58%) | 37/50 (74%) | 3/50 (6%) |

CT = computed tomography; Rad = radiography.
[1]Fractions indicate number of diagnoses based on the CT scan results relative to final diagnoses
*One cat in the group did not have radiographs.

Overall accuracy of the correct final diagnosis was higher for survey CT (42/54 (i.e., 42 cats out of 54), or a rate of 77.8%) than radiography (29/50; 58%). Cats in this study had CT imaging without sedation or anesthesia and there were no complications. The enclosure provided a suitable environment for imaging without general anesthesia or sedation and allowed constant oxygen to dyspneic cats and fluid administration throughout the procedure. In the present study, mild stair-step artifact was seen in 58% of the MPR images, however this artifact did not affect image quality or interpretation and was not noted in the lung region. CT provided additional information in 74% of the cats allowing a correct diagnosis not achieved with radiographs in 28% of cats.

The enclosure was particularly useful for dyspneic cats, who can be stressed when restrained for radiographic examination. In this study, four cats were not adequately stable for thoracic radiography study but could be imaged with CT.

Cats with pulmonary infection had the lowest number of correct diagnosis achieved with CT (2/7 cats), which could be explained by the common finding of one or multiple lung masses in this group that were misdiagnosed commonly by CT as being a primary lung tumor. The differentiation between an inflammatory from a neoplastic lung mass using CT has not been studied extensively in veterinary medicine. (In humans, diagnosis of pneumonia requires a combination of clinical assessment, radiological imaging, and appropriate microbiologic testing. CT is a valuable adjunct when thoracic radiographs are negative or nondiagnostic, in unresolved pneumonias and when complications are suspected such as when dealing with immunocompetent children, neutropenic patients, and patients with human immunodeficiency virus.) The high accuracy of CT in cats with trauma in the present study indicates that CT can be an important modality for assessing the trauma patient.

Among the seventeen cats subjected to both survey and contrast CT, the survey and contrast results lead to the same diagnosis for fifteen of the seventeen (88.2%) cats. However, nine cats had additional information provided from post-contrast images, including sternal and cranial mediastinal lymphadenopathy in eight cats, and cystic regions within a cranial mediastinal mass. In conclusion, CT was highly accurate (77.8%) for the evaluation of cats with respiratory distress. CT imaging of cats using the enclosure without general anesthesia or sedation is safe and provides more accurate diagnostic information than radiography.

In the nine cats with lung neoplasia, eight had a primary lung tumor and one had metastases from intestinal lymphoma. The most common CT findings were one to multiple lung masses (7/9), one to multiple soft-tissue nodules (4/9), pleural effusion (4/9), and a patchy alveolar pattern (4/9). Additional information obtained with CT compared with radiographs (7/9) included soft-tissue attenuating pulmonary masses (n=4, i.e., for four of the cats) and metastasis (n=4) seen either as lung nodules (n=2) or a patchy alveolar pattern (n=2). Contrast medium was given to six of the cats with lung neoplasia leading to additional CT detection of thoracic lymphadenopathy in five.

Of the nine cats with lower airway disease, seven were diagnosed based on response to therapy and follow-up, and two based on histopathology. The most common CT findings were diffuse bronchial wall thickening (8/9), a patchy alveolar pattern (5/9) and bronchiectasis (4/9). The wall of the bronchi could be easily measured and was considerably thicker compared with cats with other diseases. In a retrospective evaluation, the wall of the principal bronchi measured in 10 cats with other disease process ranged from 0.8 to 0.9 mm and bronchi could not be seen at the periphery of the pulmonary parenchyma. Additional information from survey CT compared with radiographs was obtained in eight of eight cats and included bronchial wall thickening (n=4), bronchiectasis (n=4), pneumonia (n=3), and main stem bronchial (n=2, FIG. 4) and tracheal (n=1) thickening with luminal stenosis.

Diagnoses in the nine cats with cardiomyopathy were restrictive cardiomyopathy (n=4), hypertrophic cardiomyopathy (n=3), arrythmogenic cardiomyopathy (n=1), and unclassified cardiomyopathy (n=1). The most common CT findings were cardiomegaly (7/9), pleural effusion (7/9), and a patchy alveolar pattern (6/9). Additional information was obtained from CT compared with radiographs in three of eight cats and included cardiomegaly (n=2 cats, both with pleural effusion), pleural effusion (n=1), and a consolidated alveolar pattern (n=1). Eight of nine (88.9%) cats had CT findings consistent with congestive heart failure, including pulmonary edema and pleural (n=7) or peritoneal (n=2) fluid. The interventricular septum and left ventricular free wall (average 45-68HU (Hounsfield units)) were hyperattenuating compared with blood (average 20-40HU) in survey CT images in four cats. Wall chamber characterization was indistinct in three cats and could not be assessed in two cats.

In the eight cats with a mediastinal mass, the diagnoses were thymoma (n=4), lymphoma (n=3), and carcinoma (n=1). The most common CT findings were a soft-tissue mass in the cranial mediastinum (7/8) that was homogeneous (3), cystic (3) or mixed soft tissue and mineralized (1), pleural effusion (5/8), and atelectasis (4/8). Additional information from survey CT compared with radiographs was obtained in six of seven cats and included atelectasis (n=3), and one cat each with pulmonary metastasis, sternal and cranial mediastinal lymphadenopathy, a neck mass and a lung mass. Contrast CT was performed in four cats. Additional findings in contrast-enhanced CT images were cystic portions of a thymoma (n=1) and sternal and cranial mediastinal lymphadenopathy (n=1).

Of the seven cats with infection, the diagnoses were aspiration pneumonia (n=1), suppurative tracheitis with suppurative bronchitis (n=1), suppurative tracheitis and bronchopneumonia (n=1), lung abscess with pleuritis (n=1), suppurative bronchopneumonia secondary to *Bordetella bronchiseptica* (n=1), pyogranulomatous pneumonia with fibrosis (n=1), and suppurative inflammation (n=1). The most common CT findings in this group were a patchy alveolar pattern (4/7), one to multiple lung masses (3/7), a mixed patchy and consolidated alveolar pattern (2/7) and sternal, and cranial mediastinal lymphadenopathy (2/7). Additional information was obtained with CT compared with radiographs in five of seven cats and included sternal and cranial mediastinal lymphadenopathy (n=2), and one cat each with tracheal and main stem bronchial wall thickening with stenosis and collapse, lung mass, and lung nodule. Correct diagnosis obtained with survey CT and not with radiography included pneumonia with tracheitis and tracheal and bronchial collapse and stenosis (n=1) and bronchitis with pneumonia (n=1).

Of the four cats with trauma, the diagnoses were one cat each with human abuse causing liver rupture and pulmonary contusion, tracheal rupture associated with endotracheal intubation, trapped inside a tumble clothes dryer, and hit by a car. Correct diagnosis obtained with survey CT and not with radiography were trauma (n=2) and tracheal rupture (n=1). Additional information obtained with CT (4/4) were bulla (n=1), pulmonary contusion (n=1), lung atelectasis (n=1), rib fracture (n=1), discontinuity of tracheal wall (n=1), pneumopericardium (n=1), and lung nodules (n=1).

Of the three cats with a hernia, the diagnoses included one cat each with hiatal hernia, diaphragmatic hernia, and peritoneal pericardial diaphragmatic hernia. Correct diagnosis obtained with survey CT and not with radiography was diaphragmatic hernia, radiographically diagnosed as severe pleural effusion of unknown cause. Additional information obtained with CT (1/2) included liver, spleen and fat in the thoracic cavity, and disruption of diaphragm.

Of the five cats in the miscellaneous group were cats with lidocaine toxicity, chylothorax and fibrosing pleuritis, smoke inhalation, pulmonary edema secondary to fluid overload, and normal (n=1 each). The most common CT findings were a patchy alveolar pattern (n=2), bronchial wall thickening (n=2), and one finding each of pneumothorax, pleural effusion, and bronchiectasis. Additional information obtained with CT (3/5) included: bronchial wall thickening (n=2), lung atelectasis (n=1), patchy alveolar pattern (n=1), and bronchiectasis (n=1).

None of the eight cats with primary lung neoplasia were thought to have regional lymphadenopathy based on either radiography or survey CT, however lymphadenopathy was detected in five of these cats following contrast medium administration.

CT had a higher accuracy for lower airway disease (88.9%) compared with radiography (50%), which was expected because feline lower airway disease may appear normal radiographically in as many as 23% of cats. Bronchiectasis was detected with CT in four cats but was not detected radiographically in any cat. Our results suggest that the incidence of bronchiectasis may be underestimated in cats with lower airway disease. CT had high accuracy for the diagnosis of cardiomegaly and congestive heart failure. Because radiography allowed a correct diagnosis of cranial mediastinal mass in all but one cat, the major advantage of CT imaging in these cats was in providing additional information such as lung atelectasis, pulmonary metastasis, sternal and cranial mediastinal lymphadenopathy, among others. The high accuracy of CT in cats with trauma in the present study indicates that CT can be an important modality for assessing the trauma patient. Additional details of this study are reported in "Thoracic Computed Tomography in Feline Patients Without Use of Chemical Restraint" by Oliveira et al, published 29 Mar. 2011 in Veterinary Radiology & Ultrasound, John Wiley & Sons, Inc., which is incorporated herein by reference in its entirety.

Example 4

Seventeen dogs with clinical signs attributable to nonneoplastic obstruction of the larynx, trachea, or large bronchi underwent computed tomography (CT) imaging. In 16 of the 17 dogs, CT was performed without general anesthesia, in sternal recumbency in a transparent animal restraint enclosure as described herein. All patients underwent head, neck, and thoracic CT examination using a 16-slice helical CT scanner without endotracheal tube placement. All dogs were scanned with a gantry rotation of 0.5 s.

The kVp, mA, pitch, table speed, and field of view varied based on size and movement of the patient. For brachycephalic breeds approximately 1 ml of barium paste was placed on the base of the tongue by a wooden applicator to allow better distinction between the tongue and soft palate. If severe motion artifact was observed, the CT examination was repeated. 3D internal rendering was performed using appropriate CT software. The kVP was 100 (9) or 120 (7) kVP and mA ranged from 120 to 350 (median=235). The pitch was 0.93 (n=3), 1.375 (n=6), or 1.75 (n=7) corresponding with a table speed of 9.3, 13, and 17 mm/s, respectively. The field of view was small (n=6) or large (n=10), depending on patient size. 3D internal rendering aperture varied per frame from 80 or 90 and threshold ranged from "200 to" 600HU. 3D internal rendering was needed to enable reviewers to assess laryngeal paralysis or collapse accurately, as well as to assess the arytenoids cartilages. This study showed that CT imaging of unanesthetized dogs with upper airway obstruction in a restraining device without chemical restraint is a noninvasive method of achieving a definitive diagnosis of upper airway obstruction. Additional details of this study are reported in "Computed Tomographic Imaging Of Dogs With Primary Laryngeal Or Tracheal Airway Obstruction" by Stadler et al, published 2011 in Veterinary Radiology & Ultrasound, John Wiley & Sons, Inc., which is incorporated herein by reference in its entirety.

A protocol using 80 kV, 130 mA, 0.5 s, and 0.562 pitch with 1.25 mm slice thickness, and 0.625 mm slice reconstruction interval is recommended, especially for helical thoracic CT examination of non-sedated animal patients, especially cats, examined in the enclosure 100, as excellent CT image quality has been achieved with this protocol. However, the invention is not limited in this regard and other embodiments encompass protocols as described herein. It will be understood that the specific protocols evaluated here can vary significantly with different CT machines, but that the general improvements in image quality with reduction in dosage can be achieved on such CT machines nonetheless.

Advantages provided by some embodiments of this invention include one or more of the following: allowing CT examination of non-sedated, unanesthetized cats providing a minimal to no motion artifact; 2) reduction or avoidance of artifact; and 3) improvement in the clinical environment of the imaged patient in comparison to radiography. Using the enclosure 100 for non-sedated animal patients can avoid the creation of a motion artifact in more than 10 percent of the slices during CT scan examination for about 95 percent of non-sedated animal patients, or more. In addition, the CT images retrieved are of excellent diagnostic quality, even those CT images taken during moderate or severe motion of said animals constrained within said apparatus. Further, the CT protocols with a higher pitch exhibit less motion artifact, and helical and windmill artifact are almost absent in the images acquired with 0.562 pitch. More specifically, the following protocol: 80 kV, 130 mA, 0.5 s, and 0.562 pitch with a 1.25 mm slice thickness, and a 0.625 mm slice reconstruction interval for helical thoracic CT examination of conscious (awake) animals, results in excellent CT image quality and the CT images have minor or no lung lobe atelectasis for the animals scanned without sedation or general anesthesia.

As a benefit of one or more embodiments of this invention, CT for thoracic imaging can be utilized more frequently than in the past. This is especially true with the advent of multidetector CT technology that has led to greatly decreased examination time, substantially increased longitudinal resolution by means of reduced slice thickness and slice reconstruction interval, and improved multiplanar and 3 dimensional (3-D) reconstruction. With multidetector CT scanners, isotropic pixels allow reformatted images to have the same quality as those acquired in the plane imaged directly. In pediatric CT, the high speed of multidetector CT imaging has decreased the need for sedation significantly. In veterinary medicine, use of multidetector CT scanners allows the possibility to scan sedated or awake patients.

The CT protocols disclosed herein were adapted from human pediatric CT. When performing CT imaging of awake (unsedated) cats, two similarities can be found with human pediatric CT: the need to depict very small anatomic structures, such as peripheral bronchi, and the fact that both awake cats and children often can be uncooperative patients producing motion artifact. To address these two problems we compared protocols with a low and high kV to test for differences in image contrast and with a low and high pitch to test for differences in image artifacts.

In humans, a reduction in kV is associated with an increase in image contrast. Changes in kV alter both the quality as well as the quantity of photons. By changing tube voltage, the number of photons produced changes and the photons have a different energy. It was discovered in connection with this invention that protocols with lower kV had a trend towards, but not statistically significant, higher contrast, and slightly lower SNR and CNR compared with protocols with higher kV. The higher SNR can be explained by the increased tube voltage on 120 kV, but the higher CNR in protocols with higher kV was not expected. An important consideration is the fact that the contrast measurements were performed between soft tissue and air in the lung. This contrast is not strongly dependent on kV since by definition the CT contrast scale has a difference of 1000 (HU) Hounsfield units between air and water at all kV settings. In looking at contrast or CNR between soft tissues or bone one would expect an increase or improvement at lower kV. Also in situations in which contrast media are used, the image contrast and CNR will be substantially increased at lower kV. It is well-documented in humans that besides increases in soft tissue contrast, low kV CT protocols enhance the iodine-induced contrast and thus reduces the amount of iodinated contrast media needed to image lower-weight patients, because the attenuation of iodine-based contrast media increases with reduced x-ray energy. Although statistically significant, the difference in SNR and CNR related to kV in this study was very small and probably not clinically relevant. The impact of this difference on the subjective evaluation of image quality was not assessed. The higher SNR, CNR and slightly lower noise in the protocols with 1.75 pitch can be explained by the fact that increasing pitch causes widening of the slice sensitivity profile (SSP), a measure of the ability of the CT scanner to precisely limit the information that makes up the image to a defined slice of tissue. If the individual detector collimation does not change, images acquired with higher pitch are effectively thicker slices. The slice thickness has a strong influence on the number of photons used to produce the image. Thicker slices use more photons and have better SNR. This means that the apparent advantage of higher pitch in SNR and CNR is artificial and only obtained through decrease in the longitudinal resolution.

As indicated above, patient motion can cause significant artifacts, which usually appear as shading or streaking in the reconstructed image. Motion is decreased with shorter imaging time in two ways. First, the amount of motion during each single slice acquisition decreases. Second, the ability of the patient to cooperate is improved with a shorter overall duration of the scan, at least in humans. Scan time can be decreased by using a faster gantry rotation. The scan time also affects the longitudinal (Z axis) coverage. The longitudinal coverage can be calculated by multiplying the longitudinal beam collimation, pitch, and scan time, and dividing by the gantry rotation time.

The selection of pitch is a trade-off between patient coverage and accuracy. Larger pitches reduce scanning time allowing more coverage of a patient per unit of time, but slice data must be interpolated using scan data that is farther from the actual slice, producing more artifacts. In pediatric thoracic CT although no single helical CT technique has gained universal acceptance, in general, a pitch of at least 1.3 is used and many investigators use a pitch from 1.3 to 1.6. When evaluating CT protocols for pulmonary nodule detection in dogs, pitches of 1.5 and 2 were tested and both resulted in good image quality. In evaluation of CT protocols for the cervical and lumbar spine of dogs, increasing pitch from 0 to 2 was associated with significantly poorer scores for half of the examined categories. To minimize motion artifact for the present invention, we used the fastest available rotation time (0.5 seconds) and tested protocols with higher pitch. We hypothesized that images acquired with 1.75 pitch would result in less motion artifact which was supported by the results of all evaluators. Most CT examinations judged to have moderate or severe motion artifact were obtained with protocols using 0.562 pitch. This difference was expected since the scan time using 1.75 pitch was approximately 30% of the scan time using 0.562 pitch. However, even though a statistically significant difference was found between high and low pitch for motion artifact, overall, motion artifact was considered to be absent or minimal for the majority of examinations regardless of protocol and moderate or severe motion were present in a very small percentage of examinations. Furthermore, all images were considered of excellent diagnostic quality, even those ranked as having moderate or severe motion. Finally, all CT examinations were ranked by the worse score present, regardless of number of slices affected. In this regard, only 5% (4/80) of the examinations had motion artifact present in more than 10% of the total number of slices.

Liver margins were considered consistently blurred on the low pitch protocols, but the degree of blurring was very mild and did not seem to affect the overall image quality.

Although protocols with a higher pitch had less motion artifact, substantial helical and windmill CT artifacts were found using these protocols with a moderate to good interobserver agreement. Helical and windmill artifact were significant in most images with 1.75 pitch and these artifacts were almost absent in the images acquired with 0.562 pitch.

It is a common understanding that the windmill artifact is due to the need for data interpolation in helical scanning Generally, the amplitude of the windmill artifact decreases as the number of detector rows increases: the windmill artifact in 64-slice is less than in 16-slice CT. Both windmill and helical artifacts gradually increase as pitch is increased. As helical pitch increases, the number of detector rows intersecting the image plane per rotation increases and the number of "vanes" in the windmill artifact increases, but the strength of the artifact in each vane decreases proportionately. The most recommended practice to avoid this artifact is to scan using the thinnest possible individual detector collimation, in other words, fine longitudinal sampling, and reconstructing thick images, such as 1 and 2 mm or thicker images. For example, a detector collimation of 16×0.625 mm is preferable to 16×1.25 mm or 8×2.5 mm. Obtaining thicker images than the individual detector collimation is equivalent to longitudinal filtering, which means a substantial compromise on the longitudinal resolution, but also a decrease in image noise.

Near isotropic images could be acquired by reformatting the 0.625 mm slice thickness images in dorsal and sagittal planes for the thorax and dorsal and transverse planes for the head. Recent advances in multidetector CT technology have made the acquisition of isotropic data feasible with use of a narrow configuration of the detector array so that only the smallest detector elements are exposed. Through several generations of CT scanners, long-axis resolution was consistently inferior to short-axis, or transverse, spatial resolution. Spatial resolution in the transverse plane is limited by pixel size. Within a matrix of 512×512 and a scanning field of view of 25 cm, the pixels that constitute each axial image are squares with a length of approximately 0.49 mm on each side. Using the "detail" reconstruction algorithm, the spatial resolution due to the algorithm is about 0.6 mm. Thus, a slice thickness in the range of 0.5-0.8 mm is required to achieve similar spatial resolution in all three dimensions. If the thickness of the axial slice is taken into account, the square pixels are converted to three dimensional voxels. When data are reconstructed to achieve similar dimensions in all 3 planes it consists of cube-shaped voxels and the images are considered to be isotropic. Isotropic imaging minimizes the importance of patient positioning and obviates the need to obtain transverse, dorsal and sagittal planes directly because reformation in any desired plane will have a spatial resolution similar to that of the original plane. This is especially important when imaging awake cats since the original images are acquired in a nontraditional oblique plane depending on the position of the cat inside the apparatus.

Since the cats were scanned without sedation or general anesthesia the CT scan images showed no lung lobe atelectasis in all but one cat, in which atelectasis probably occurred as a result of recumbency.

When developing the protocols disclosed herein, information from the technical data sheet of the CT scanner to adjust the scan parameter was used to provide substantially the same CTDIvol (volume computed tomography dose index) for each of the four protocols used. When performing the scans the CTDIvol generated by the CT scanner were recorded and the displayed results were in fact similar for all 4 protocols. The CT Dose Index (CTDI) is the dose measured in a 16 or 32 cm acrylic phantom (the CTDI phantom), while the CTDIvol is a weighted average of surface and central dose measurements in the phantom so as to approximate the average dose to the phantom volume when the effect of pitch on dose is also taken into account. The CTDIvol is widely used in human adult and pediatric CT to evaluate different protocols on a single CT scanner since an initial comparison of different techniques can be easily performed.

Although positive, the correlation found between body weight and noise, and width of the chest and noise was very weak and probably not clinically relevant. This correlation could be explained by the fact that cats in this study had a wide range of body weight and thoracic cavity width and this could increase image noise if tube current and voltage are not changed. If the noise increases and contrast and signal intensity do not increase proportionally, it is expected that CNR and SNR will vary in the opposite direction.

The mean total time in the CT scanner in this study was similar to time to perform a 3-view thoracic study in a cooperative cat with experienced holders, which is on average 10 minutes. However, in a clinical situation when only one protocol would be used the total time in the CT scanner when scanning awake cats would be significantly reduced. Furthermore, CT examinations were believed to be less stressful for the cats, since no direct manipulation was necessary, and safer for personnel due to the absence of radiation exposure.

The measurements of $FiO_2$ inside the apparatus could have been affected by the fact that some cats turned around constantly resulting in temporary blocking of the flow of oxygen. Although motion artifact was almost absent, some cats were scanned multiple times when the images were initially considered non-diagnostic. When dealing with an uncooperative patient, the advantages of performing CT without general anesthesia, such as the possibility to scan a patient that otherwise would not be submitted to CT due to clinical instability, absence of lung atelectasis, and faster and less expensive examinations, could be considered a trade-off with the potential radiation hazard and increased tube usage that could result from multiple scans.

During the CT scan the regions of interest (head or thorax) were not at the isocenter of the CT machine since pre-scan scouts were not made and it was not possible to know where the cat would be positioned inside the enclosure. This could have been responsible, at least in part, for some image degradation.

The enclosure disclosed herein provides effective oxygen and catheter-based therapy while keeping safe temperature and $CO_2$ levels, and allows CT imaging of sedated, unanesthetized cats. Coupled with a 16-slice CT scanner, the enclosure allowed whole-body images to be successfully acquired in a very short period of time with excellent spatial resolution in all three planes and negligible motion artifact. Presumed lung lobe atelectasis was present in only one cat and deemed to be very mild. Protocols with 1.75 pitch had significant windmill and helical artifact that compromised image quality and therefore are not recommended. With 0.562 pitch, windmill and helical artifacts were almost absent and motion, although statistically higher compared to 1.75 pitch, was overall minimal and not considered to be clinically relevant, Based on these results, we recommend a protocol of 80 kV, 130 mA, 0.5 s, and 0.562 pitch with a 1.25 mm slice thickness, and a 0.625 mm slice reconstruction interval for helical thoracic CT examination of awake cats using the apparatus. Protocol adjustments for cats with different body weights and conformations do not seem to be necessary. The enclosure has the potential to make a significant impact on the safety of the diagnostic imaging and case management of cats with respiratory compromise.

The terms "first," "second," and the like, herein do not denote any order, quantity, or importance, but rather are used to distinguish one element from another. The terms "a" and "an" herein do not denote a limitation of quantity, but rather denote the presence of at least one of the referenced item.

Although the invention has been described with reference to particular embodiments thereof, it will be understood by one of ordinary skill in the art upon a reading and understanding of the foregoing disclosure that numerous variations and alterations to the disclosed embodiments will fall within the scope of this invention and of the appended claims.

What is claimed is:

1. An enclosure comprising:
   an open base structure; and
   a lid which is configured to substantially close the base structure when the lid is in a closed position on the base structure, the lid being movable from the closed position to an open position to permit the introduction of an animal patient into the base structure;
   wherein the base structure or the lid has at least one open-ended slot which is partially obstructed when the lid is in the closed position, and
   wherein the base structure or the lid has at least one aperture which is not obstructed when the lid is in the closed position; and
   wherein the base structure comprises a base member having a semi-cylindrical configuration and wherein the lid has a semi-cylindrical configuration, so that when the lid is in the closed position, the base member and the lid cooperate to define a substantially cylindrical space;
   wherein the base structure includes a footing for stably supporting the base member on a flat surface; and
   wherein the enclosure is substantially X-ray transparent.

2. The enclosure of claim 1 wherein the enclosure has at least one aperture suitable to provide gas flow into the enclosure.

3. The enclosure of claim 1 wherein the base member has a first base end panel, and a second base end panel, one of the first and second base end panels having a slot therein;
   the lid has a first lid end panel, and a second lid end panel;
   at least one of the first lid end panel and the second lid end panel is configured to partially obstruct the slot.

4. The enclosure of claim 1 wherein the enclosure is substantially visually transparent.

5. The enclosure of claim 1 having a diameter of 20 to 40 cm and a length of about 40 cm.

6. A veterinary CT scan apparatus comprising:
   a CT scan gantry or sensor ring;
   a CT scan table, and
   a substantially X-ray transparent animal restraint enclosure comprising an open, concave base structure and a concave lid which is configured to substantially close the base structure and define a cylindrical space between them when the lid is in a closed position on the base structure, the lid being movable from the closed position to an open position;
   wherein the base structure or the lid has at least one open-ended slot which is partially obstructed when the lid is in the closed position, and
   wherein the base structure or the lid has at least one aperture which is not obstructed when the lid is in the closed position.

7. A method of performing a CT scan on an animal patient in a CT scan apparatus having a patient target position to produce CT scan image results of the animal patient, the method comprising:
   placing the animal patient in a substantially X-ray transparent open base structure;
   placing a concave substantially X-ray transparent lid on the open base structure to form an animal restraint enclosure having a cylindrical space between the lid and the base structure;
   placing the animal within the restraint enclosure in the patient target position for the CT scan; and
   conducting the CT scan;
   wherein the base structure or the lid has at least one open-ended slot which is partially obstructed when the lid is in the closed position, and wherein the base structure or the lid has at least one aperture which is not obstructed when the lid is in the closed position.

* * * * *